(12) United States Patent
Mori et al.

(10) Patent No.: US 9,709,586 B2
(45) Date of Patent: Jul. 18, 2017

(54) AUTOMATIC ANALYZER (71) Applicant: Hitachi High-Technologies Corporation, Tokyo (JP)

(72) Inventors: Takamichi Mori, Tokyo (JP); Kazuhiro Nakamura, Tokyo (JP); Yoshihiro Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/413,286

(22) PCT Filed: Jul. 8, 2013

(86) PCT No.: PCT/JP2013/068583
§ 371 (c)(1),
(2) Date: Jan. 7, 2015

(87) PCT Pub. No.: WO2014/017276
PCT Pub. Date: Jan. 30, 2014

(65) Prior Publication Data
US 2015/0192600 A1    Jul. 9, 2015

(30) Foreign Application Priority Data

Jul. 27, 2012 (JP) ................ 2012-166493

(51) Int. Cl.
*G01N 35/10* (2006.01)
(52) U.S. Cl.
CPC ..... *G01N 35/1004* (2013.01); *G01N 35/1016* (2013.01); *G01N 2035/1018* (2013.01)

(58) Field of Classification Search
CPC ............... G01N 35/10; G01N 35/1002; G01N 35/1004; G01N 35/1006; G01N 35/1009; B01L 3/02; B01L 3/0217; B01L 3/0279
See application file for complete search history.

(56) References Cited

U.S. PATENT DOCUMENTS 3,800,984 A * 4/1974 Phelan .................. 422/509
6,022,747 A    2/2000 Gherson et al.
(Continued)

FOREIGN PATENT DOCUMENTS

JP    06-109745 A    4/1994
JP    07-198726 A    8/1995
(Continued)

*Primary Examiner* — Brian R Gordon
(74) *Attorney, Agent, or Firm* — Mattingly & Malur, PC (57) ABSTRACT

To provide an automatic analyzer which is not influenced by fluidity or viscosity of a sample, and which can stably dispense the sample with dispensing accuracy by determining whether a flow route including a sample probe is in a stable and suction-available state when the sample is suctioned. In suction of the sample, before the sample is suctioned, in the flow route including the sample probe, the automatic analyzer determines whether the sample is in a suction-available state or in a suction-unavailable state, and performs cleaning on the flow route when it is determined that the sample is not in the suction-available state. Since the state in the flow route including the sample probe is determined before the sample is suctioned, the automatic analyzer can repeatedly perform a dispensing operation having improved reliability, without being influenced by the fluidity or the viscosity.

3 Claims, 6 Drawing Sheets (56) References Cited

U.S. PATENT DOCUMENTS

| | | | | |
|---|---|---|---|---|
| 6,370,942 | B1* | 4/2002 | Dunfee | G01M 3/26 |
| | | | | 73/1.74 |
| 6,521,187 | B1* | 2/2003 | Papen | B01L 3/0268 |
| | | | | 222/263 |
| 8,257,664 | B2* | 9/2012 | Ogusu | G01N 35/1016 |
| | | | | 422/501 |
| 8,435,738 | B2* | 5/2013 | Holmes | G01N 33/50 |
| | | | | 422/68.1 |
| 2004/0159675 | A1* | 8/2004 | Nishino | B01L 3/0227 |
| | | | | 222/135 |
| 2008/0317639 | A1* | 12/2008 | Shimoda | G01N 35/1016 |
| | | | | 422/400 |
| 2009/0041628 | A1* | 2/2009 | Kakizaki | G01N 35/1004 |
| | | | | 422/68.1 |
| 2009/0075386 | A1* | 3/2009 | Dunfee | G01N 35/1009 |
| | | | | 436/54 |
| 2009/0266149 | A1* | 10/2009 | Kaplit | G01N 35/1016 |
| | | | | 73/54.09 |
| 2011/0232397 | A1* | 9/2011 | Schenk | 73/864.13 |
| 2014/0220693 | A1* | 8/2014 | Yamazaki | G01N 35/1016 |
| | | | | 436/54 |
| 2014/0290341 | A1* | 10/2014 | Subramanian | G01N 35/1004 |
| | | | | 73/37 |
| 2015/0323557 | A1* | 11/2015 | Tamezane | G01N 35/1009 |
| | | | | 422/67 |

FOREIGN PATENT DOCUMENTS

| | | |
|---|---|---|
| JP | 11-083868 A | 3/1999 |
| JP | 11-271324 A | 10/1999 |
| JP | 2000-39440 A | 2/2000 |
| JP | 2007-113979 A | 5/2007 |

* cited by examiner

AUTOMATIC ANALYZER

TECHNICAL FIELD

The present invention relates to a sample dispensing device for dispensing a liquid sample such as blood or urine and an automatic analyzer using the same, and particularly relates to an automatic analyzer which can accurately detect clogging in suction and discharge sample probes.

BACKGROUND ART

For example, an automatic analyzer such as a biochemical automatic analyzer or an immunological automatic analyzer includes a sample dispensing device which automatically suctions a liquid sample from a sample container and discharges the liquid sample to a reaction container (hereinafter, referred to as dispensing).

The sample dispensing device includes a sample probe, a dispensing syringe connected thereto, and a mechanism for moving the sample probe to a predetermined position. The sample dispensing device is configured to repeatedly perform a dispensing operation in which a distal end of the sample probe is inserted into a sample, and the dispensing syringe is driven by a predetermined amount. In this manner, a predetermined amount of the sample is suctioned, then the sample probe is moved to the reaction container, and the suctioned sample is discharged.

Incidentally, in a laboratory test such as a specimen test, a blood cell, a serum, and plasma are frequently used as the sample. If these are left neglected for a long time from collection until the test, a solid material (hereinafter, referred to as a clot) such as a fibrin thrombus is generated in the sample. If the sample is loaded into the automatic analyzer as it is, the generated clot clogs the sample probe in some cases. If the clogging occurs in the sample probe as described above, a predetermined amount of the sample cannot be dispensed to the reaction container, and thus an accurate analysis result cannot be obtained. This results in greatly damaged analysis reliability in the automatic analyzer.

As means for solving this disadvantageous problem, many inventors have proposed those which detect the clogging of the sample probe based on pressure variations by disposing pressure sensor inside a dispensing flow route including the sample probe. According to PTL 1, a value obtained through the secondary differentiation of a pressure variation waveform is focused on, and the value is compared with a threshold value In this manner, abnormal suction can be detected without being influenced by the viscosity. In addition, PTL 2 adopts a configuration in which residual pressure remaining on a negative side is focused on, and the clogging is determined when the residual pressure is lower than the threshold value, after the suction operation is completed. Furthermore, PTL 3 discloses a technology which determines abnormality during sample dispensing, based on a comparison between an area value obtained by integrating an output of the pressure sensor and a predetermined reference value. In addition, PTL 4 discloses a configuration which includes detection means for detecting the clogging of a sampling nozzle, and in which a sample analysis operation is stopped when severe clogging occurs.

Citation List

PATENT LITERATURE

PTL 1: JP-A-7-198726
PTL 2: JP-A-11-83868
PTL 3: JP-A-2000-39440
PTL 4: JP-A-6-109745

SUMMARY OF INVENTION

Technical Problem

When a sample having high viscosity, such as a blood cell, is suctioned by using a dispensing syringe via a sample probe, there are some difficulties to determine clogging by using a pressure sensor during suction and after suction. If the viscosity of the blood cell is compared to the viscosity of glycerin, the viscosity of the blood cell is 60% to 100% of the viscosity of the glycerin. When the sample having the high viscosity is suctioned, as the viscosity becomes higher, it takes more time to return pressure between the sample probe and the pressure sensor to atmospheric pressure after the sample is suctioned. It is desirable that considerable waiting time be affordable after the suction. However, this leads to degraded processing capabilities, and thus this method is not pragmatic.

It is also possible to cope with this problem by giving an allowable margin to a threshold value for determining the clogging. However, when the sample having the high viscosity is suctioned, regardless of normal suction, a case of determining that clogging occurs can be assumed.

In addition, a method may also be selected so as not to check the clogging when the sample having the high viscosity is dispensed. However, when the sample having the high viscosity is continuously suctioned and discharged and the clogging occurs in the middle thereof, the sample is unintentionally scattered to a range of a rotation trajectory of the sample probe. If the scattered sample enters a reaction container to which the sample is not originally supposed to be discharged, an automatic analyzer loses its reliability.

In addition, according to the technology disclosed in PTL 4, when serious clogging occurs, a sample analysis operation is stopped. Since it is necessary to remove the clogging one time, a dispensing operation cannot be performed continuously.

An object of the present invention is to provide an automatic analyzer which can stably maintain dispensing accuracy even in case of a sample having high viscosity by checking clogging removing inside a sample probe prior to sample suction and by performing clogging removing and cleaning operations.

Solution to Problem

In order to achieve the above-described object, configurations of the present invention are adopted as follows.

There is provided an automatic analyzer having a liquid sample dispensing mechanism which includes a sample probe, a syringe that suctions a liquid sample from and discharges the liquid sample to the sample probe, a dispensing flow route that connects the sample probe and the syringe to each other, cleaning solution supply means for supplying cleaning solution into a flow route leading from the dispensing flow route into the sample probe and for cleaning the inside of the sample probe, a cleaning solution flow route that connects the cleaning solution supply means and the syringe to each other, and an electromagnetic valve that opens and closes the cleaning solution flow route. A state of a flow route system including the inside of the sample probe is examined before the liquid sample is suctioned, and based on an examination result of the flow route system, it is determined whether the liquid sample is in a suction-available state, or whether the liquid sample is in a suction-unavailable state and is in a state of requiring flow route cleaning.

Even in a case where the clogging occurs, clogging removing and cleaning operations enable the suction in a state where the clogging inside the sample probe is always removed before the sample is suctioned.

In addition, a cleaning operation is performed after the sample is suctioned, and an examination prior to suction is performed each time before the sample is suctioned. Accordingly, it is possible to perform the cleaning operation for removing the clogging prior to full clogging. Therefore, it is possible to realize a stable dispensing operation.

Advantageous Effects of Invention

According to the present invention, clogging is not present or in a removed state inside a sample probe at all times before a sample is suctioned. Therefore, it is possible to perform dispensing continuously and stably without being influenced by the viscosity of the sample.

In addition, a state inside the sample probe is examined every cycle before the sample is suctioned, and clogging removing and cleaning operations are performed when necessary. Accordingly, it is possible to realize a stable sample dispensing operation by preventing the clogging. Therefore, it is possible to improve reliability of dispensing accuracy by preventing the dispensing accuracy from being degraded due to the clogging.

DESCRIPTION OF EMBODIMENTS

Hereinafter, an embodiment of the present invention will be described with reference to the drawings.

Figure 1:
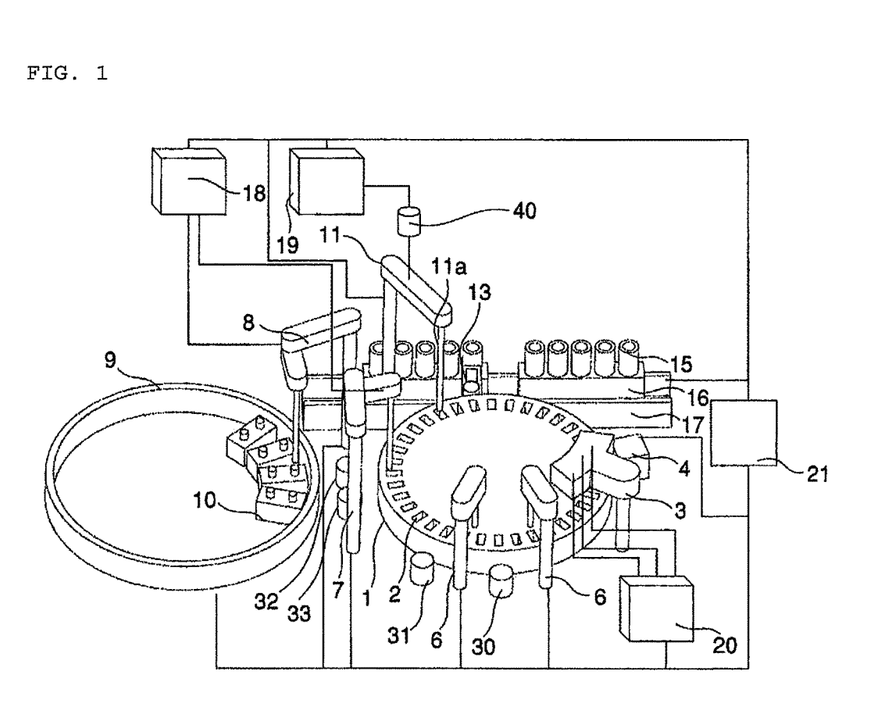
FIG. 1 is a schematic view of an automatic analyzer according to the present invention.

FIG. 1 is a schematic view of an automatic analyzer according to the embodiment of the present invention; Since a function of each unit is known, detailed description will be omitted. Reaction containers 2 are circumferentially arrayed side by side on a reaction disk 1. Multiple reagent bottles 10 can be circumferentially placed inside a reagent disk 9. A sample conveying mechanism 17 which moves a rack 16 having a sample container 15 placed thereon is installed close to the reaction disk 1. Reagent dispensing mechanisms 7 and 8 are installed between the reaction disk 1 and the reagent disk 9. A sample dispensing mechanism 11 which is rotatable and vertically movable is installed between the reaction disk 1 and the sample conveying mechanism 17, and a sample probe 11a is provided therein. Sample syringes 19 are respectively connected to the sample probe 11a. The sample probe 11a moves while drawing a circular arc around a rotary shaft, and dispenses a sample from the sample container to a reaction cell. A pressure sensor 40 detects pressure in a flow route inside the sample probe.

A cleaning mechanism 3, a spectrophotometer 4, stirring mechanisms 5 and 6, the reagent disk 9, and the sample conveying mechanism 17 are arranged around the reaction disk 1, and a cleaning pump 20 is connected to the cleaning mechanism 3. Cleaning tanks 13, 30, 31, 32, and 33 are respectively installed on an operation range of the reagent dispensing mechanisms 7 and 8, the sample dispensing mechanism 11, and the stirring mechanisms 5 and 6. A reagent syringe 18 is connected to the reagent dispensing mechanisms 7 and 8. A test sample such as blood is contained in the sample container 15, is placed on the rack 16, and is conveyed by the sample conveying mechanism 17. In addition, each mechanism is connected to a controller 21. Hitherto, configurations of the automatic analyzer have been described.

Next, an embodiment according to the present application will be described.

Figure 4A:
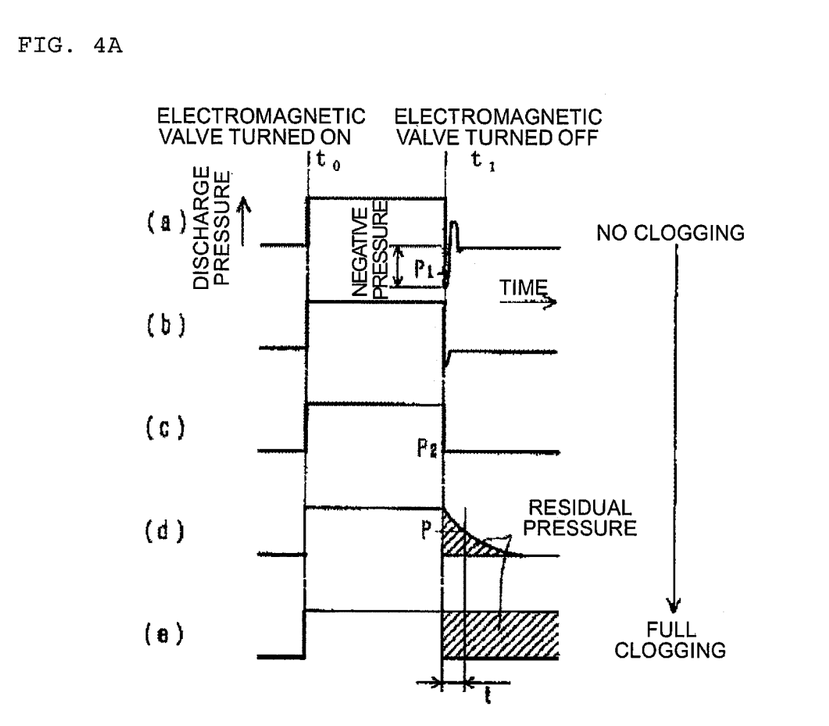
FIG. 4A is a view illustrating variations in a negative pressure peak value and a residual pressure value depending on a degree of nozzle clogging.

FIG. 4A illustrates variations in a waveform of discharge pressure depending on a clogged degree of the sample probe 11a in the pressure sensor 40, that is, illustrates variations in a negative pressure peak value and a residual pressure value. FIG. 4A illustrates a case where a temporal transition is represented by a horizontal axis, discharge pressure becomes constant by turning on an electromagnetic valve inside the sample syringe 19 and causing cleaning water to flow therein at time $t_0$, and the discharge pressure varies from (a) to (e) depending on the clogged degree of the sample probe 11a by turning off the electromagnetic valve inside the sample syringe 19 at time $t_1$. For simple illustration, atmospheric pressure is set to zero in FIG. 4A.

First, when the clogging of the sample probe 11a is absent, as illustrated in (a), the discharge pressure immediately after the electromagnetic valve is turned off at time $t_1$ and does not become zero quickly, becomes negative pressure $P_1$ once due to inertial force of the cleaning water, and becomes zero after slightly swinging. Then, if the clogged degree of the sample probe 11a becomes severe and the sample probe 11a is closed, as illustrated in (b), resistance increases inside the sample probe 11a, and the inertial force of the cleaning solution in a flow route decreases. Consequently, the negative pressure peak value decreases in size. If the clogged degree of the sample probe 11a becomes more severe, as illustrated in (c), the negative pressure becomes zero ($P_2$). According to the above-described (a) to (c), when the negative pressure is zero or greater, it can be considered that dispensing accuracy of the sample probe 11a is tentatively in a reliable range.

If the clogged degree of the sample probe 11a becomes further severe and the sample probe 11a is progressively closed, as illustrated by an oblique line in (d), residual pressure is generated. If the clogged degree of the sample probe 11a becomes still further severe and the sample probe 11a is fully closed, as illustrated by an oblique line in (e), the discharge pressure cannot return to zero, and the residual pressure does not vary while maintaining a constant value.

Figure 2:
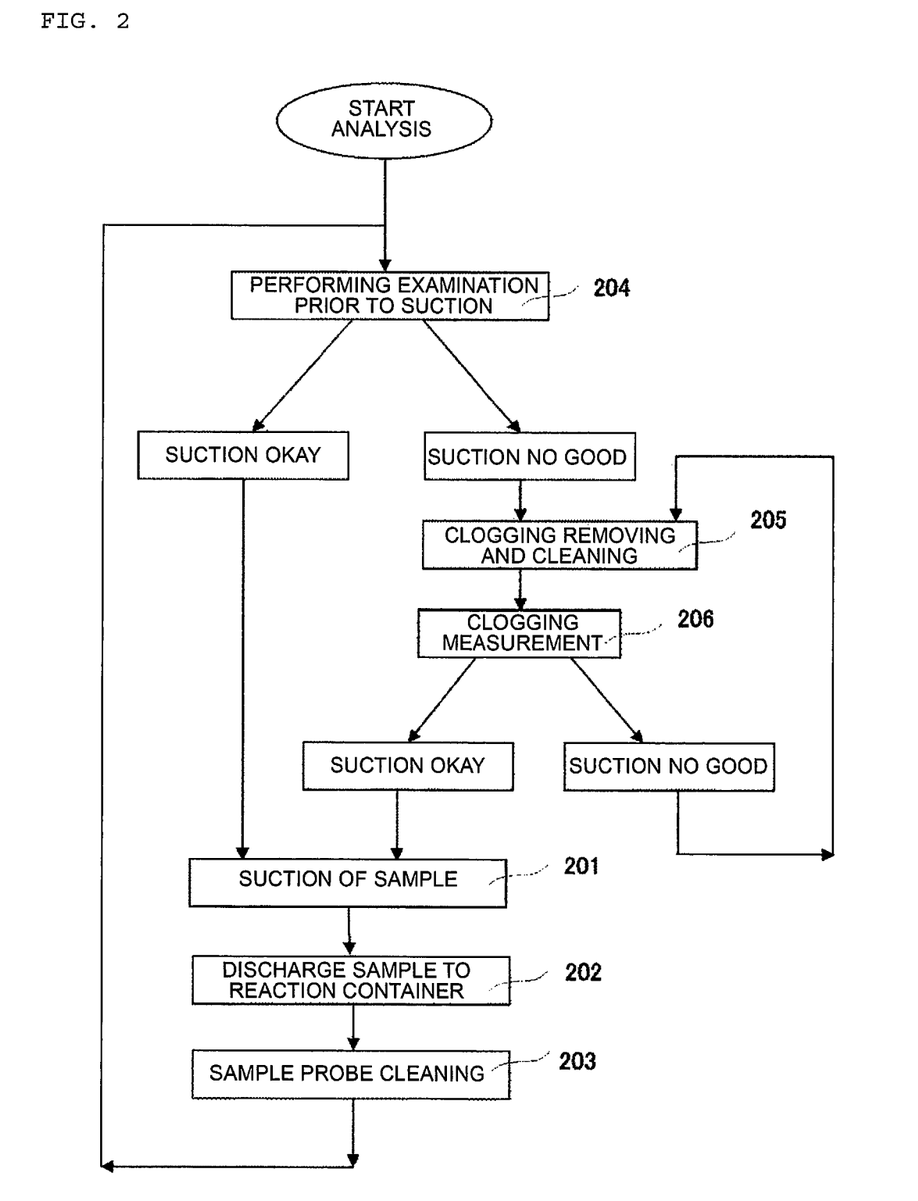
FIG. 2 is a diagram illustrating clogging measurement flow.

Here, when an analysis starts as illustrated in FIG. 2, an examination on whether the clogging is present or not inside the sample probe 11a is performed before a liquid sample is suctioned. An examination method is configured so that cleaning 203 inside the sample probe 11a is performed using the cleaning tank 13 by turning on an electromagnetic valve 35, the electromagnetic valve 35 is turned off after a predetermined time period elapses, and the pressure inside the sample probe 11a returns to the atmospheric pressure within a predetermined time period (t). Alternatively, a time period required for returning to the atmospheric pressure is measured (examination prior to suction 204). Unless a case shows the state illustrated by (d) and (e) in FIG. 4A, that is, in a case of (a), (b), and (c) in FIG. 4A, it is determined as normal. After it is determined as "suction okay", the dispensing operation starts for the next specimen. Here, the "suction okay" indicates a state where the clogging removing operation is not needed, and "suction no good" indicates a state where the clogging removing operation is needed, which is illustrated in the case of (d) and (e) in FIG. 4. This can determine whether the pressure returns to the atmospheric pressure within the above-described predetermined time period, or using the time period required for returning to the atmospheric pressure.

Figure 4B:
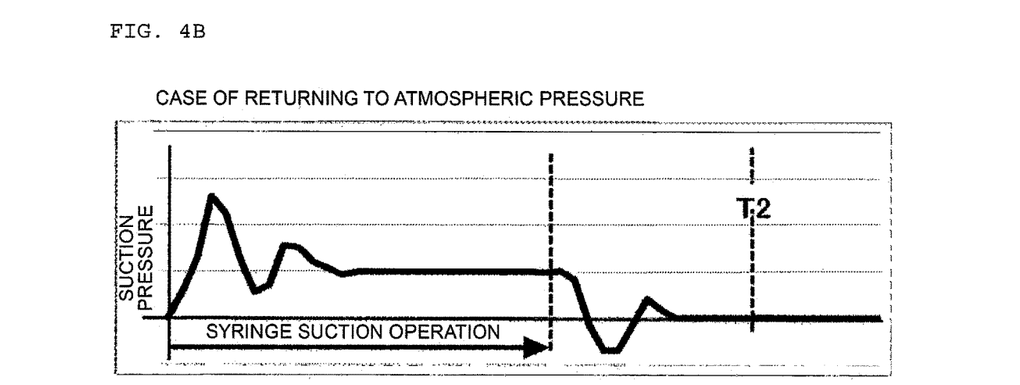
FIG. 4B is a view illustrating variations in the residual pressure value after a syringe suctions air.
Figure 4C:
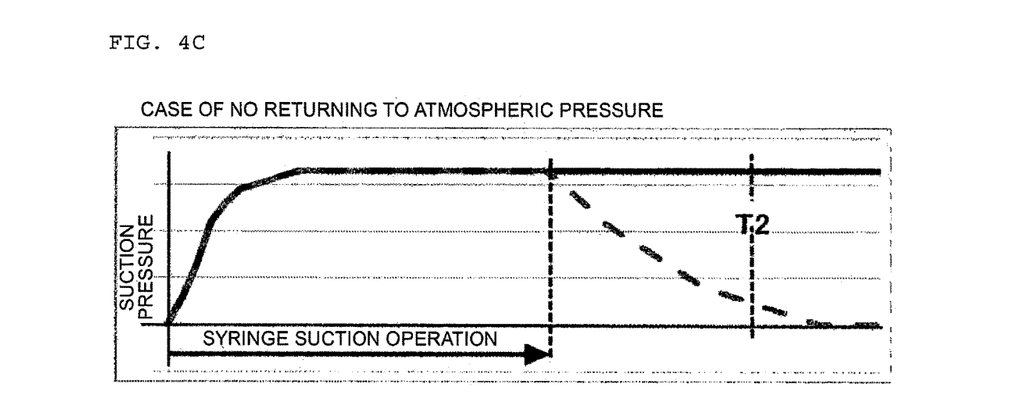
FIG. 4C is a view illustrating variations in the residual pressure value after the syringe suctions the air.

Alternatively, in the examination prior to suction in FIG. 2, the air is suctioned by using the sample syringe 19 after the inside of the sample probe 11a is cleaned and then the electromagnetic valve 35 is turned off. After the air suction operation is performed by the sample syringe 19, if the clogging is absent in the sample probe 11a, as illustrated in FIG. 4B, the pressure inside the sample probe 11a returns to the atmospheric pressure at time T2. As illustrated in FIG. 4C, in a case (solid line) where the pressure does not return to the atmospheric pressure at time T2, when the pressure cannot return to the atmospheric pressure until time T2, although there is a case (broken line) where the pressure gradually returns to the atmospheric pressure, it is determined as "suction no good" in the examination prior to suction 204. The air permeates a distal end portion of the sample probe 11a by the air suction operation, but the distal end is filled with water by turning on the electromagnetic valve 35 after the clogging measurement is performed. Accordingly, there is no possibility that the air may cause the device to have the degraded processing speed. In both FIGS. 4B and 4C, the horizontal axis represents the time, and a range indicated by an arrow represents a range of the time when the syringe suction operation is performed. In addition, time T2 is set after the syringe suction operation is completed and a certain time period elapses. It is possible to determine (examine) whether the clogging is present or absent by detecting the pressure at time T2.

As described above, before the liquid sample is suctioned, a state of a flow route system including the inside of the sample probe 11a is examined. Based on an examination result of the flow route system, it is possible to determine whether the liquid is in a suction-available state ("suction okay"), or whether the liquid is in a suction-unavailable state and the flow route is in a state of requiring the cleaning ("suction no good"). It is desirable to examine the state in the flow route system without fail before the liquid sample is suctioned.

When the pressure is determined as "suction no good" after the electromagnetic valve 35 is turned off, an operation for clogging removing and cleaning 205 is performed. Even when it is determined as "suction no good", the device does not stop the analysis. The operation for the clogging removing and cleaning 205 is performed by allocating one cycle of dispensing cycles to the operation for the clogging removing and cleaning 205, thereby minimizing degradation of the device processing capability. In the clogging removing and cleaning 205, the cleaning water is discharged from the inside of the sample probe, and the pressure of the cleaning water removes the clogging. As described above, when it is determined that the liquid sample cannot be suctioned ("suction no good"), based on the examination result of the state in the flow route system including the inside of the sample probe before the liquid is suctioned, the flow route system including the inside of the sample probe is controlled so as to return to a normal state. For example, in this control for returning the flow route system to the normal state, a control unit 50 repeatedly performs suction and discharge operations using the syringe while operating the electromagnetic valve 35 which opens and closes a cleaning solution flow route.

Sample probe cleaning 203 in the usual sample probe 11a requires the time for rotation and a vertical operation of the sample probe 11a. Accordingly, as compared to the operation of the clogging removing and cleaning 205, the time for cleaning consumed is less. In contrast, when the clogging removing and cleaning 205 is performed, the sample probe 11a does not perform at least a rotational operation from a position of the cleaning tank 13. Accordingly, it is possible to set more cleaning time for the clogging removing and cleaning 205. The reason for this is that the sample probe 11a is on standby at the position of the cleaning tank 13 until clogging measurement 206 is completed.

Furthermore, the clogging measurement 206 is performed after the clogging removing and cleaning 205. This reason is to check whether the clogging is removed by performing the clogging removing and cleaning 205. In a case of "suction okay", the process is controlled so as to suction the sample. In contrast, in a case of "suction no good", the clogging removing and cleaning 205 is performed again. Even when the clogging is removed again, the time of one cycle may be entirely allocated to the clogging removing and cleaning 205. Alternatively, the repeated clogging removing and cleaning 205 may be settled within one cycle by shortening the time for the clogging removing and cleaning 205 so that the repeated clogging removing and cleaning 205 is also settled within one cycle.

Figure 3:
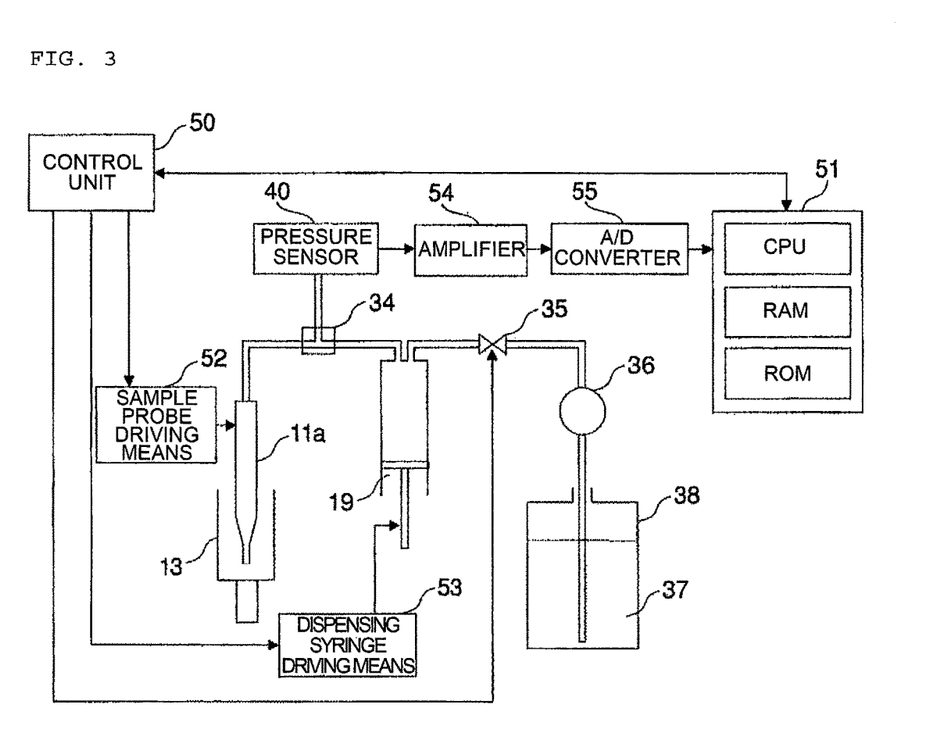
FIG. 3 is a detail view illustrating a cleaning method.

FIG. 3 illustrates details of a cleaning method. FIG. 3 is a view illustrating cleaning solution supply means for cleaning from a dispensing flow route to the inside of the sample probe . The sample syringe 19 serves to suction and discharge the liquid sample from and to the sample probe 11a, and the dispensing flow route for connecting both of these is present between the sample syringe 19 and the sample probe 11a. The dispensing flow route is branched to the pressure sensor 40 side by a branching block 34. A pressure signal detected by the pressure sensor 40 is connected to an A/D converter 55 via an amplifier 54 so as to be transmitted to a microcomputer 51 as the pressure signal. The microcomputer 51 communicates with the control unit 50 so as to control sample probe driving means 52, dispensing syringe driving means 53, and the electromagnetic valve 35. Cleaning water 37 is supplied to the sample probe 11a in such a way that the electromagnetic valve 35 is turned on and off so as to control the opening and closing of the cleaning solution flow route, thereby enabling a pump 36 to pump the cleaning water 37. As illustrated in FIG. 3, the pump 36 applies high pressure to the inside of the sample probe 11a at the position of the cleaning tank 13 and the electromagnetic valve 35 is turned on. In this manner, the sample inside the sample probe 11a is extracted to perform the cleaning, and the measurement 206 for removing the clogging is performed after the electromagnetic valve 35 is turned off. Alternatively, in order to perform the dispensing without stopping the device, it is also effective to select a method in which the sample syringe 19 performs an air suction operation, and when it is determined here again as "suction no good", the operation for clogging removing and cleaning 205 is repeatedly performed as illustrated in FIG. 2, and in which the operation for clogging removing and cleaning 205 is repeatedly performed until the measurement 206 for removing the clogging shows "suction okay".

In addition, as a method of the clogging removing and cleaning 205, the following method can be employed.

The first method is performed in such a way that the electromagnetic valve 35 is turned on for a certain time period in a state where the pump 36 maintains high pressure. In this operation, as described above, more time can be used in the clogging removing and cleaning 205 as compared to the usual sample probe cleaning 203. Accordingly, the first method is effectively employed in order to remove the clogging inside the sample probe 11a.

The, second method is also effectively employed since the electromagnetic valve 35 is repeatedly turned on and off, and pressure is applied to the clogging foreign matter using pulsations so that the clogging matter is pressed outward from the sample probe 11a. Here, the turning-on time and the turning-off time for the electromagnetic valve 35 may be configured so that the turning-on time is equal to the turning-off time, the turning-off time is longer than the turning-on time, or the turning-on time is longer than the turning-off time. In addition, the number of repeated turning on and off of the electromagnetic valve 35 is not particularly limited, and may be appropriately set in advance, as long as the pressure can be decreased by turning on the electromagnetic valve 35 within the time until the pressure is returned to a predetermined pressure by closing the electromagnetic valve 35, and within the time which can be consumed for the operation of the clogging removing and cleaning 205.

In addition, these two methods may be used in combination with each other. For example, when it is necessary to repeatedly perform the operation for the clogging removing and cleaning 205 since it is determined as "suction no good" based on the examination prior to suction 204, the combined method is configured so that constant high pressure is applied for the first time (first method) and the pressure is applied using the pulsations by turning on and off the electromagnetic valve 35 for the second time (second method). In addition, if the third time is needed, a method is also considered in which for the third time, the operation for the clogging removing and cleaning 205 is performed at the turning-on time and the turning-off time of the electromagnetic valve 35 which are different from those for the second time. When the operation for the clogging removing and cleaning 205 is performed multiple times, it is desirable to change the method for the clogging removing and cleaning 205 on each occasion. The reason is that there may be a case where an effect cannot be expected by performing the operation for the same clogging removing and cleaning 205 since it is determined as "suction no good" once. If multiple methods are employed, the more excellent effect can be expected in the clogging removing. Therefore, in the repeated cleaning of the flow route system including the inside of the sample probe, It is desirable that the electromagnetic valve is controlled differently each time repeated cleaning is performed. The meaning of changing the method for the clogging removing and cleaning 205 includes not only the meaning of changing the above-described method, but also the meaning of changing a pressure value of the high pressure using the first method and the meaning of changing the turning-on time and the turning-off time of the electromagnetic valve 35 using the second method.

The third method is performed in such a way that while a high pressure state is maintained by the pump 36 and the electromagnetic valve 35 is turned on for a certain time period, the sample syringe 19 suctions the air to reach the maximum suction amount so as to perform an operation for discharging a suctioned volume increased by the maximum suction amount. Alternatively, there is a method of repeatedly performing the suction and discharge operations of the sample syringe 19 during the cleaning using the pump 36. In this method, in addition to high pressure extracting from the pump 36 which is added to the above-described first method, the discharge pressure of the sample syringe 19 is also applied thereto. Accordingly, the method can effectively remove the clogging foreign matter.

As another application example, the following may be considered. The pressure waveform illustrated in FIGS. 4A and 4B is acquired for each cycle by the cleaning operation after the dispensing is completed. In this regard, the device stores a waveform during the clogging measurement 204 when the device starts to use a new product of the sample probe 11a. For example, if it is determined as the state of (c) in FIG. 4A, the device issues an alarm to notify a user of the replacement time of the sample probe 11a. Alternatively, when it is determined as the state of (c) in FIG. 4A, before the sample probe 11a is fully clogged, one or more cycles are allocated to the operation for the nozzle removing and cleaning 205 so that the sample probe 11a can be continuously brought into dispensing-available state. This method is effectively employed in improving the reliability of the device.

Figure 5:
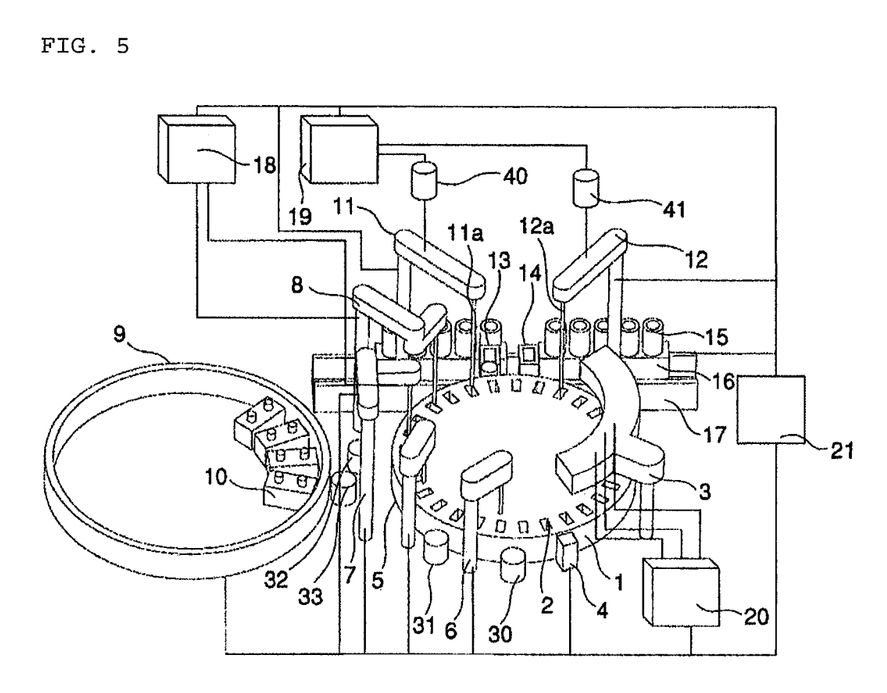
FIG. 5 is a schematic general view of an automatic analyzer having two sample probes.

Hitherto, an example has been described in which various samples are dispensed by a single sample probe. Hereinafter, an example will be described in which two sample suction sample probes are mounted on the device. As illustrated in FIG. 5, the sample probe 11a is a sample probe which exclusively dispenses a sample such as plasma and urine. A sample probe 12a dispenses blood cells and whole blood which have high viscosity and are likely to cause clogging, and the sample probe 12a is exclusively used for measuring HbA1c. Even when the occurrence of the clogging is determined by the clogging measurement 204 in the sample probe 12a and the operation for the nozzle removing and cleaning 205 is repeatedly performed, the sample probe 11a can continue the dispensing operation. Accordingly, the device can continue to perform the analysis without stopping the measurement.

It is desirable that a user of the device can set the number of cleanings for the repetition number N of the, nozzle removing and cleaning 205 of the sample probe 12a. It is assumed that the rack 16 is present at a suction position of the sample probe 12a as illustrated in FIG. 5, and the sample probe 12a performs the operation for the nozzle removing and cleaning 205 by detecting the clogging during the dispensing. If the first time operation for the nozzle removing and cleaning 205 does not settle the clogging and thus the flow in FIG. 2 is repeatedly progressed, the rack 16 present at the suction position of the sample probe 11a cannot move to the next movement position and is left in a standby state. In this case, the sample probe 11a can dispense the sample without any problem. Consequently, this causes the device to have the degraded processing capability. Therefore, it is desirable that the user of the device optionally preset the number of cleanings (N) by enabling the user to repeatedly clean the flow route system including the inside of the sample probe.

In addition, a dispensing request using the sample probe 12a is known in advance. Accordingly, after it is determined as "clogging removing no good" in the sample probe 12a, the number of the repeated cleanings to be performed until the next dispensing request using the sample probe 12a is started may be set to the maximum repetition number N for the nozzle removing and cleaning 205.

In addition, as the method of setting the number of cleanings, for example, a method of setting the number of cleanings which completes the operation for the nozzle removing and cleaning 205 of the sample probe 12a after the sample prove 11a stands by, for example, during the maximum three cycles is also effectively employed. At this time, the sample probe 12a cannot return to the operation for the nozzle removing and cleaning 205. While an alarm is issued and the measurement is cancelled, the sample probe 11a is brought into an analysis-available state. During that time, the sample probe 11a continuously performs the analysis. While the sample probe 12a performs the operation for the nozzle removing and cleaning 205, the rack 16 just passes through the position of the sample probe 12a without performing the dispensing. However, while the sample probe 11a is operated, the sample probe 12a may be caused to repeatedly perform the operations for the nozzle removing and cleaning 205 and the clogging measurement 206. In this manner, after the clogging measurement 206 after the nozzle removing and cleaning. 205 enables the user to confirm that the foreign matter is removed, the device returns to the usual operation. Accordingly, without cancelling all the dispensing requests, the sample probe 12a can measure a specimen which is located in the device and is requested for the measurement. For example, at a stage where the foreign matter is removed, the alarm can be cancelled. Alternatively, the device can notify an operator of information indicating that the alarm is cancelled.

In addition, during the nozzle removing and cleaning 205, the pressure value is measured each time. Accordingly, the device stores the waveform of the pressure when the first time operation for the nozzle removing and cleaning 205 is completed. As compared to the first time, if there is no change in the waveform of the pressure after the operation for the nozzle removing and cleaning 205 which is posterior to the N-th time, the device completes the operation for the nozzle removing and cleaning 205 so as to cancel the dispensing of the sample probe 12a. In this manner, the operator may also set the repetition number N.

Hitherto, an example has been described in which the clogging measurement 204 is performed after the cleaning of the sample probe 11a (12a). However, the clogging measurement 204 when the sample probe 11a (12a) suctions the sample is performed in addition to the clogging measurement 204 after the cleaning. In this manner, it is possible to confirm whether the sample probe 11a (12a) is enabled to normally suction the sample. In addition, the clogging measurement 204 is performed during the cleaning of the sample probe 11a (12a). In this manner, it is possible to confirm whether the sample probe 11a (12a) is enabled to normally discharge the sample to the reaction-container. It is possible to improve the dispensing reliability of the device by confirming these during the sample suction or during the cleaning of the sample probe 11a (12a).

Referring to FIG. 5, the clogging measurement and the clogging removing and cleaning in the sample probe 12a have been described. However, the operation for the clogging removing and cleaning 205 maybe performed in the sample probe 11a, and is not limited to the sample probe 12a.

REFERENCE SIGNS LIST 1 reaction disk
2 reaction container
3 cleaning mechanism
4 spectrophotometer
5 stirring mechanism
6 stirring mechanism
7 reagent dispensing mechanism
8 reagent dispensing mechanism
9 reagent disk
10 reagent bottle
11 sample dispensing mechanism
11a sample probe
12 sample dispensing mechanism
12a sample probe
13 cleaning tank
14 cleaning tank
15 sample container
16 rack
17 sample conveying mechanism
18 reagent syringe
19 sample syringe
20 cleaning pump
21 controller
30 cleaning tank
31 cleaning tank
32 cleaning tank
33 cleaning tank
34 branching block
35 electromagnetic valve
36 pump
37 cleaning water
38 water supply tank
40 pressure sensor
50 control unit
51 microcomputer
52 sample probe driving means
53 dispensing syringe driving means
54 amplifier
55 A/D converter
201 suction operation
202 discharge operation
203 sample probe cleaning
204 examination prior to suction
205 clogging removing and, cleaning
206 clogging measurement

The invention claimed is:

1. An automatic analyzer comprising:
a reaction disk;
a plurality of reaction containers disposed on the reaction disk;
a spectrophotometer;
a sample probe driving means;
a sample probe connected to the sample probe driving means to drive the sample probe;
a syringe that suctions a sample of blood cells or whole blood from a sample container of a plurality of sample containers into the sample probe and discharges the sample of blood cells or whole blood from the sample probe into a reaction container;
a syringe means for driving the syringe;
a cleaning solution tank holding a cleaning solution;
a flow route including:
    a dispensing flow route that connects the sample probe and the syringe to each other;
    a cleaning solution flow route that connects the cleaning solution tank and the syringe;
    an internal probe route inside the sample probe;
an electromagnetic valve disposed on the cleaning solution flow route that opens and closes the cleaning solution flow route;
a control unit;

a pressure sensor disposed on the dispensing flow route and configured to measure a time-series of pressure within the dispensing flow route and output a measurement result signal indicating the pressure to the control unit, wherein the control unit is connected to the spectrophotometer, sample probe driving means, the syringe driving means, electromagnetic valve, and pressure sensor, and is programmed to:

control the electromagnetic valve and the syringe drive means to drive the syringe and open and close the electromagnetic valve thereby causing the cleaning solution to flow into the sample probe to clean the sample probe, after the cleaning solution flows into the sample probe:

control the sample probe driving means and syringe driving means to cause the sample probe to suction air and simultaneously control the pressure sensor to measure a time-series of pressure within the dispensing flow route, determine whether the sample probe has a clog based on whether the pressure of the time-series of pressure returns to a predetermined pressure after a predetermined amount of time elapses, and when the sample probe is determined to not have the clog, control the sample probe driving means and syringe driving means to cause the sample probe to suction the sample of blood cells or whole blood from the sample container and discharge the sample into the reaction container.

2. The automatic analyzer according to claim 1, wherein the control unit is programmed to:

when the sample probe is determined to have the clog, control the syringe driving means and electromagnetic valve to repeatedly suction and discharge cleaning solution while opening and closing the electromagnetic valve.

3. The automatic analyzer of claim 1, wherein the control unit is further programmed to:

after determining whether the sample probe has the clog and before the sample probe driving means and syringe driving means cause the sample probe to suction the sample of blood cells or whole blood from the sample container, control the electromagnetic valve and the syringe drive means to suction the cleaning solution into a distal end of the sample probe from the cleaning solution tank, wherein the cleaning solution is water.

* * * * *